(12) United States Patent
Ortiz et al.

(10) Patent No.: US 7,771,440 B2
(45) Date of Patent: Aug. 10, 2010

(54) METHOD AND APPARATUS FOR ENDOSCOPICALLY PERFORMING GASTRIC REDUCTION SURGERY IN A SINGLE PASS

(75) Inventors: Mark S. Ortiz, Milford, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1211 days.

(21) Appl. No.: 11/206,297

(22) Filed: Aug. 18, 2005

(65) Prior Publication Data
US 2007/0043384 A1    Feb. 22, 2007

(51) Int. Cl.
*A61B 17/10* (2006.01)
(52) U.S. Cl. ............... 606/142; 606/139; 606/143; 606/144; 227/175.1
(58) Field of Classification Search ......... 606/139–144, 606/153; 227/175.1
See application file for complete search history.

(56) References Cited

U.S. PATENT DOCUMENTS

| | | | | |
|---|---|---|---|---|
| 4,603,693 A | * | 8/1986 | Conta et al. ............ | 227/179.1 |
| 4,789,090 A | * | 12/1988 | Blake, III .............. | 227/19 |
| 4,841,888 A | * | 6/1989 | Mills et al. ............ | 112/169 |
| 4,927,428 A | * | 5/1990 | Richards ............... | 606/148 |
| 4,990,153 A | * | 2/1991 | Richards ............... | 606/148 |
| 5,080,663 A | | 1/1992 | Mills et al. | |
| 5,139,513 A | * | 8/1992 | Segato ................ | 606/219 |
| 5,242,457 A | | 9/1993 | Akopov et al. | |
| 5,282,807 A | * | 2/1994 | Knoepfler .............. | 606/143 |
| 5,306,281 A | * | 4/1994 | Beurrier ............... | 606/144 |
| 5,355,897 A | * | 10/1994 | Pietrafitta et al. ........ | 128/898 |
| 5,376,101 A | | 12/1994 | Green et al. | |
| 5,383,880 A | * | 1/1995 | Hooven ................ | 606/142 |
| 5,437,681 A | | 8/1995 | Meade et al. | |
| 5,439,156 A | * | 8/1995 | Grant et al. ............ | 227/179.1 |
| 5,462,558 A | | 10/1995 | Kolesa et al. | |
| 5,514,159 A | | 5/1996 | Matula et al. | |
| 5,540,705 A | | 7/1996 | Meade et al. | |
| 5,564,615 A | * | 10/1996 | Bishop et al. ........... | 227/175.1 |
| 5,571,119 A | | 11/1996 | Atala | |
| 5,628,446 A | * | 5/1997 | Geiste et al. ............ | 227/175.1 |
| 5,709,693 A | * | 1/1998 | Taylor ................ | 606/145 |
| 5,713,910 A | | 2/1998 | Gordon et al. | |
| 5,814,071 A | | 9/1998 | McDevitt et al. | |
| 5,853,416 A | * | 12/1998 | Tolkoff ................ | 606/140 |
| 6,036,694 A | * | 3/2000 | Goble et al. ............ | 606/304 |
| 6,059,719 A | | 5/2000 | Yamamoto et al. | |

(Continued)

FOREIGN PATENT DOCUMENTS

EP    1545336    6/2005

(Continued)

*Primary Examiner*—Todd E Manahan
*Assistant Examiner*—Erin Colello

(57) ABSTRACT

A gastric reduction apparatus provides for the secure attachment of multiple fasteners into the gastric wall, the fasteners being linked with a flexible member in a manner permitting the reduction of the effective size of an individual's stomach. The apparatus includes an applicator head including a proximal end and a distal end. The applicator head of the gastric reduction apparatus includes a cavity shaped and dimensioned for receiving tissue. A fastener attachment mechanism is positioned within the cavity for access to tissue that is pulled within the cavity and the fastener attachment mechanism includes a plurality of fasteners.

23 Claims, 7 Drawing Sheets

U.S. PATENT DOCUMENTS

| | | | |
|---|---|---|---|
| 6,126,058 A * | 10/2000 | Adams et al. | 227/180.1 |
| 6,346,111 B1 * | 2/2002 | Gordon et al. | 606/144 |
| 6,352,503 B1 * | 3/2002 | Matsui et al. | 600/104 |
| 6,443,962 B1 | 9/2002 | Gaber | |
| 6,454,778 B2 * | 9/2002 | Kortenbach | 606/144 |
| 6,494,888 B1 | 12/2002 | Laufer et al. | |
| 6,506,196 B1 | 1/2003 | Laufer | |
| 6,558,400 B2 * | 5/2003 | Deem et al. | 606/151 |
| 6,572,629 B2 * | 6/2003 | Kalloo et al. | 606/151 |
| 6,656,194 B1 | 12/2003 | Gonnoe et al. | |
| 6,663,639 B1 | 12/2003 | Laufer et al. | |
| 6,702,826 B2 * | 3/2004 | Liddicoat et al. | 606/151 |
| 6,716,222 B2 * | 4/2004 | McAlister et al. | 606/139 |
| 6,719,763 B2 * | 4/2004 | Chung et al. | 606/144 |
| 6,719,764 B1 | 4/2004 | Gellman et al. | |
| 6,743,169 B1 * | 6/2004 | Green et al. | 600/204 |
| 6,746,460 B2 | 6/2004 | Gannoe et al. | |
| 6,755,338 B2 * | 6/2004 | Hahnen et al. | 227/175.1 |
| 6,755,843 B2 * | 6/2004 | Chung et al. | 606/139 |
| 6,773,440 B2 * | 8/2004 | Gannoe et al. | 606/142 |
| 6,835,200 B2 | 12/2004 | Laufer et al. | |
| 6,908,427 B2 * | 6/2005 | Fleener et al. | 600/104 |
| 6,923,819 B2 | 8/2005 | Meade et al. | |
| 7,063,715 B2 * | 6/2006 | Onuki et al. | 606/220 |
| 7,140,528 B2 * | 11/2006 | Shelton, IV | 227/175.4 |
| 7,208,005 B2 * | 4/2007 | Frecker et al. | 606/205 |
| 7,261,722 B2 * | 8/2007 | McGuckin et al. | 606/139 |
| 7,351,201 B2 * | 4/2008 | Ouchi et al. | 600/104 |
| 2001/0023352 A1 | 9/2001 | Gordon et al. | |
| 2002/0042621 A1 | 4/2002 | Liddicoat et al. | |
| 2002/0107530 A1 * | 8/2002 | Sauer et al. | 606/139 |
| 2002/0107531 A1 * | 8/2002 | Schreck et al. | 606/142 |
| 2003/0065358 A1 * | 4/2003 | Frecker et al. | 606/205 |
| 2003/0083674 A1 | 5/2003 | Gibbens, III | |
| 2003/0093117 A1 | 5/2003 | Saadat | |
| 2003/0120289 A1 * | 6/2003 | McGuckin et al. | 606/151 |
| 2003/0171760 A1 | 9/2003 | Gambale | |
| 2003/0181924 A1 | 9/2003 | Yamamoto et al. | |
| 2003/0181929 A1 * | 9/2003 | Geitz | 606/151 |
| 2003/0208209 A1 * | 11/2003 | Gambale et al. | 606/144 |
| 2003/0233104 A1 * | 12/2003 | Gellman et al. | 606/139 |
| 2003/0233108 A1 | 12/2003 | Gellman et al. | |
| 2004/0034369 A1 * | 2/2004 | Sauer et al. | 606/139 |
| 2004/0044354 A1 | 3/2004 | Gannoe et al. | |
| 2004/0059350 A1 | 3/2004 | Gordon et al. | |
| 2004/0082963 A1 | 4/2004 | Gannoe et al. | |
| 2004/0088008 A1 | 5/2004 | Gannoe et al. | |
| 2004/0122473 A1 | 6/2004 | Ewers et al. | |
| 2004/0138682 A1 | 7/2004 | Onuki et al. | |
| 2004/0147941 A1 | 7/2004 | Takemoto et al. | |
| 2004/0147958 A1 | 7/2004 | Lam et al. | |
| 2004/0162568 A1 * | 8/2004 | Saadat et al. | 606/139 |
| 2004/0172047 A1 | 9/2004 | Gellman et al. | |
| 2004/0194790 A1 | 10/2004 | Laufer et al. | |
| 2004/0210243 A1 | 10/2004 | Gannoe et al. | |
| 2004/0217146 A1 * | 11/2004 | Beck | 227/176.1 |
| 2004/0260344 A1 | 12/2004 | Lyons et al. | |
| 2005/0015101 A1 | 1/2005 | Gibbens, III et al. | |
| 2005/0055038 A1 * | 3/2005 | Kelleher et al. | 606/151 |
| 2005/0070931 A1 | 3/2005 | Li et al. | |
| 2005/0075653 A1 | 4/2005 | Saadat et al. | |
| 2005/0263562 A1 * | 12/2005 | Shelton et al. | 227/176.1 |
| 2006/0022015 A1 * | 2/2006 | Shelton et al. | 227/176.1 |
| 2006/0025811 A1 * | 2/2006 | Shelton, IV | 606/205 |
| 2006/0025812 A1 * | 2/2006 | Shelton, IV | 606/205 |
| 2006/0025816 A1 * | 2/2006 | Shelton, IV | 606/215 |

FOREIGN PATENT DOCUMENTS

| | | |
|---|---|---|
| EP | 1569709 | 9/2005 |
| EP | 1584295 A2 * | 10/2005 |
| EP | 1586275 A2 * | 10/2005 |
| EP | 1639936 A1 * | 3/2006 |
| GB | 1327022 | 8/1973 |
| WO | WO0061012 | 10/2000 |
| WO | WO01/10312 | 2/2001 |
| WO | WO0166001 | 9/2001 |
| WO | WO0189393 | 11/2001 |
| WO | WO02/35980 | 5/2002 |
| WO | WO 02/096327 | 12/2002 |
| WO | WO 03/105670 | 12/2003 |
| WO | WO 2005/020802 | 3/2005 |

* cited by examiner

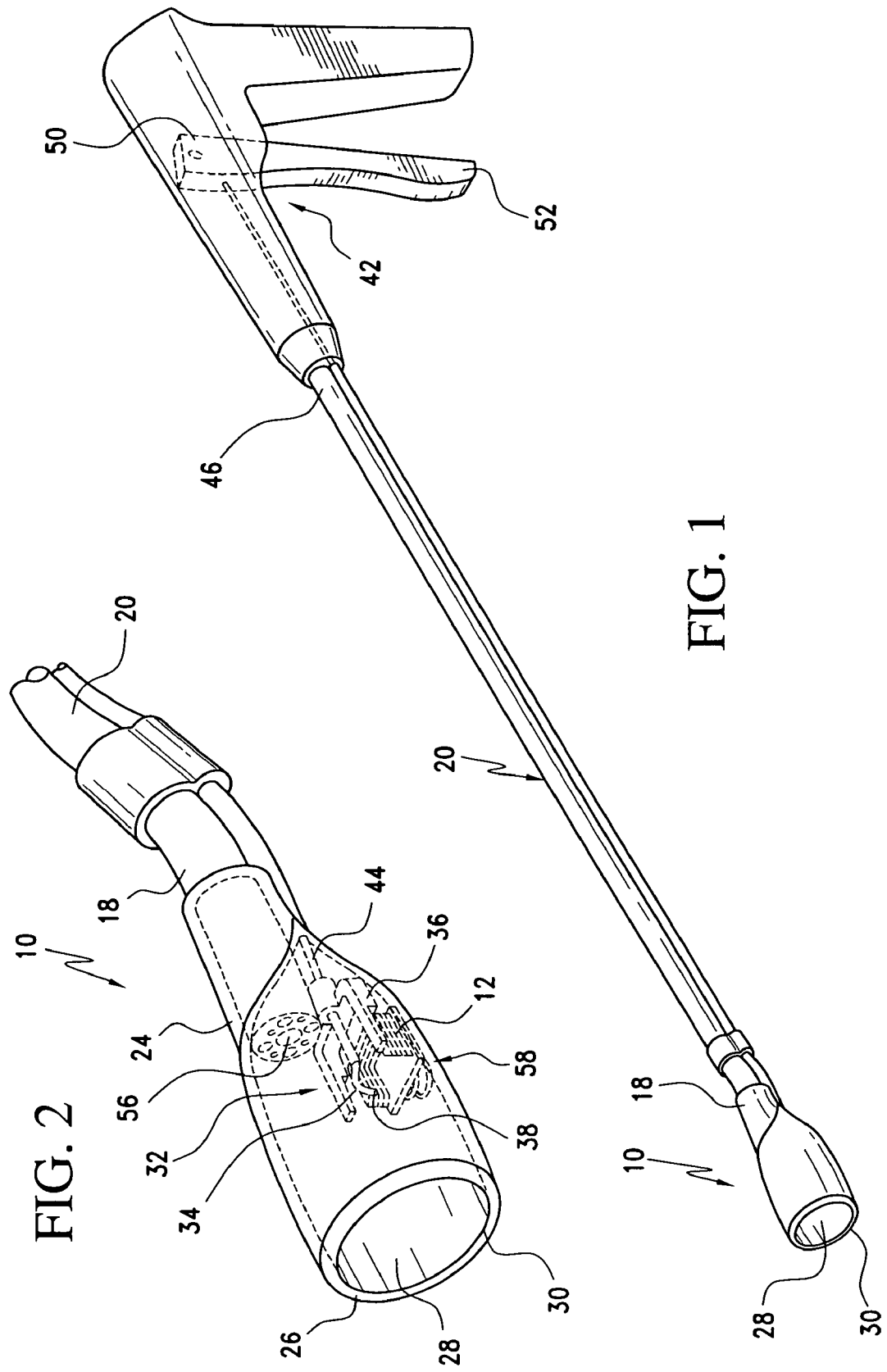

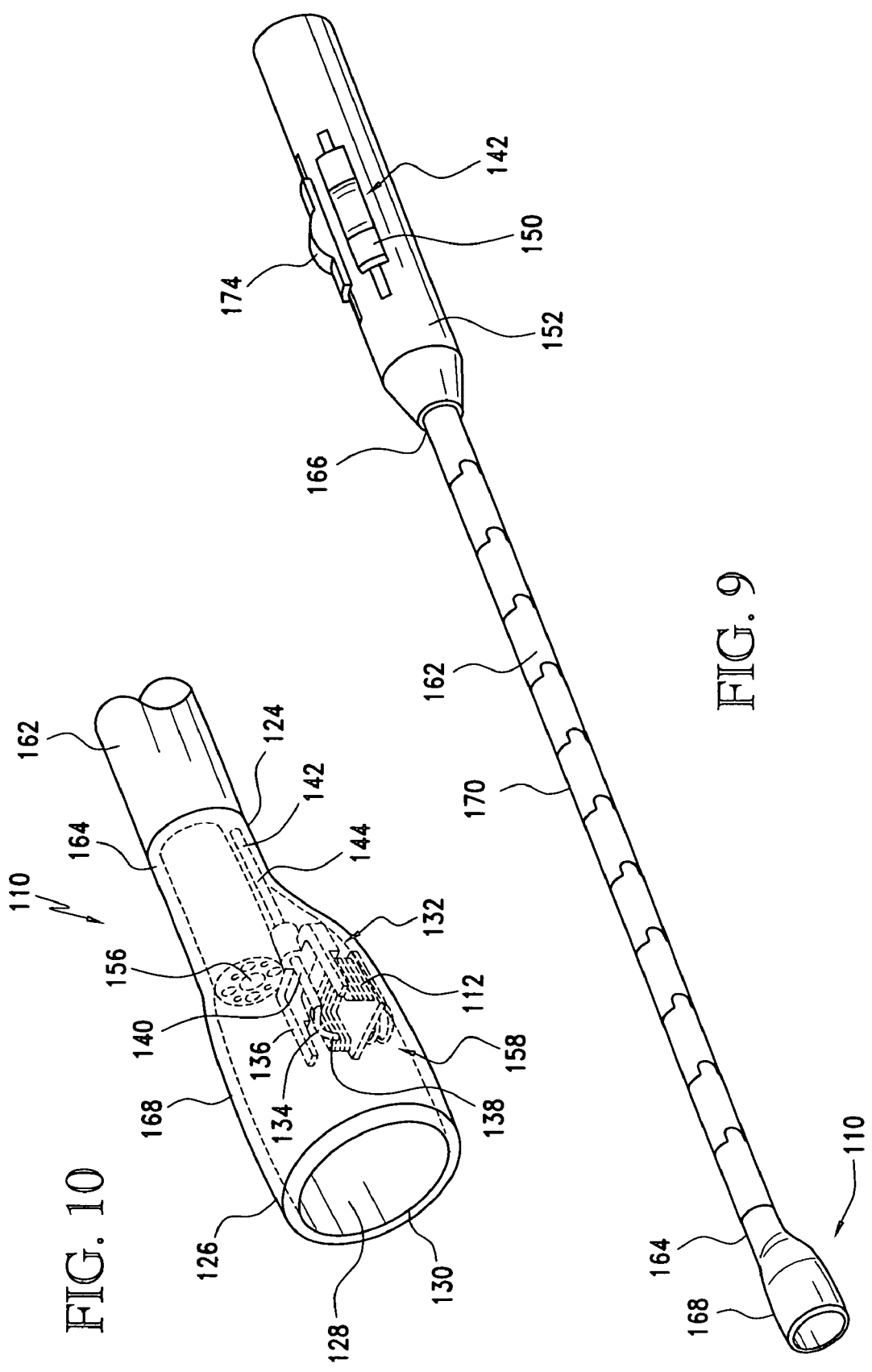

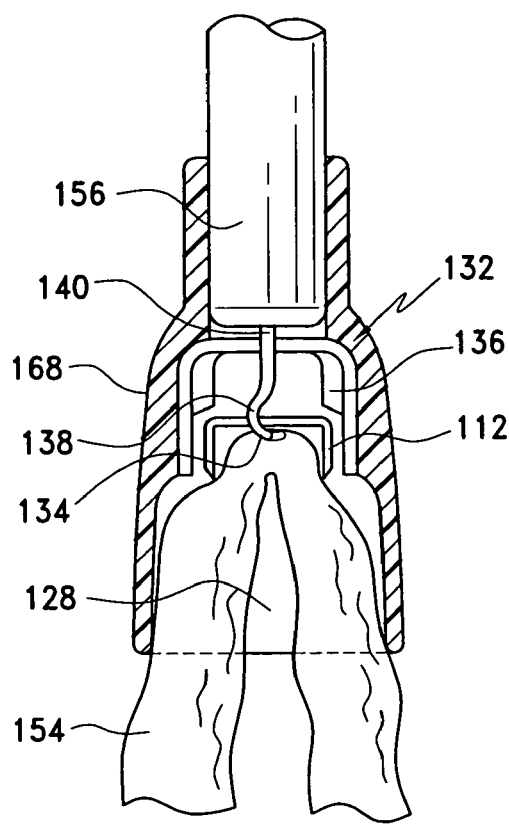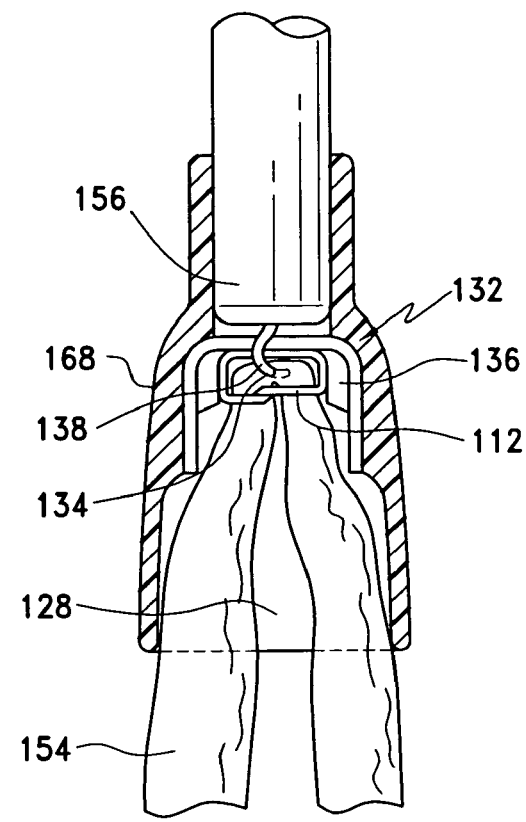
FIG. 11   FIG. 12
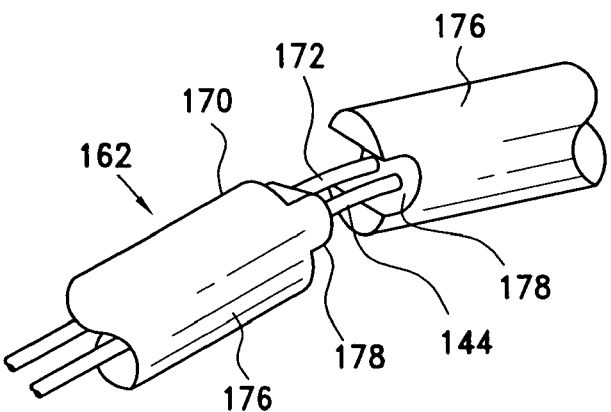
FIG. 14
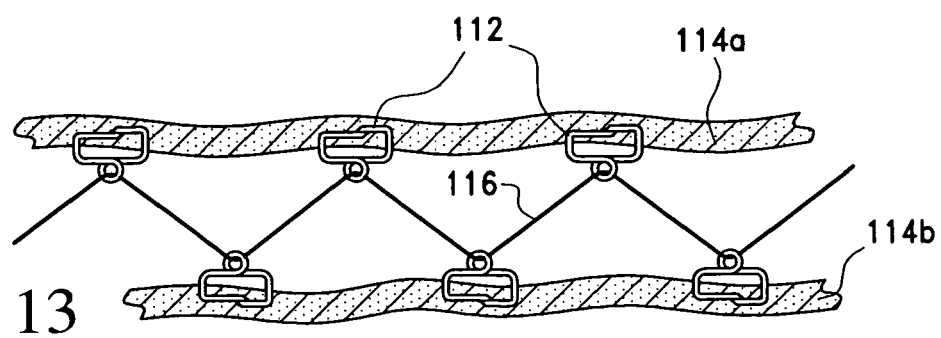
FIG. 13

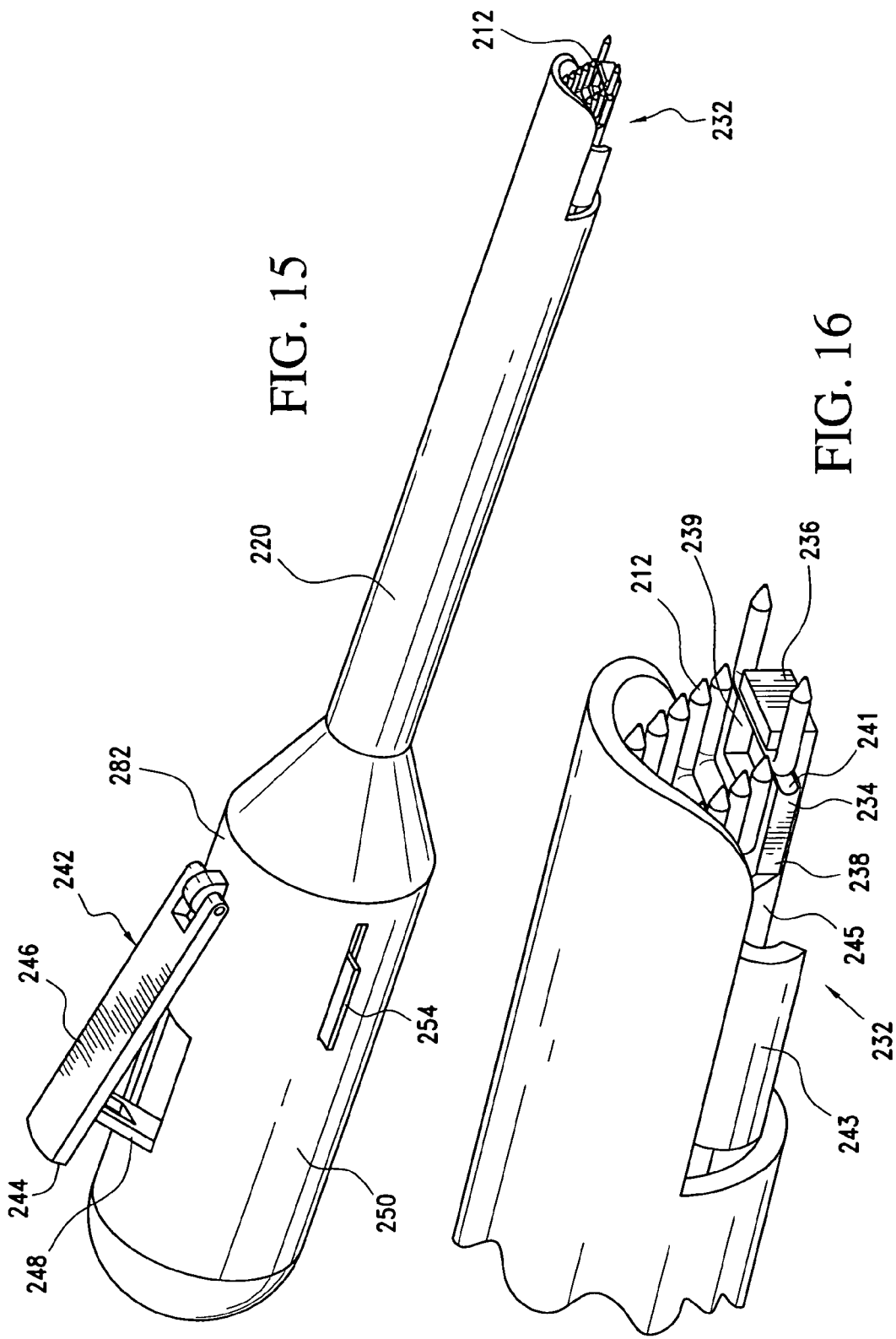

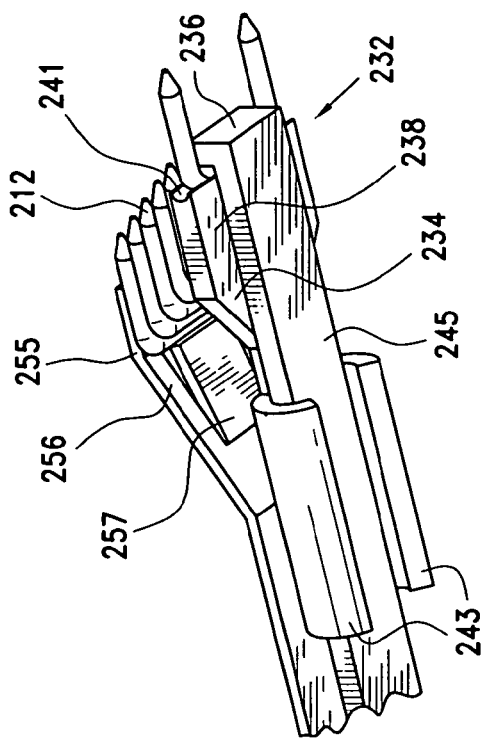
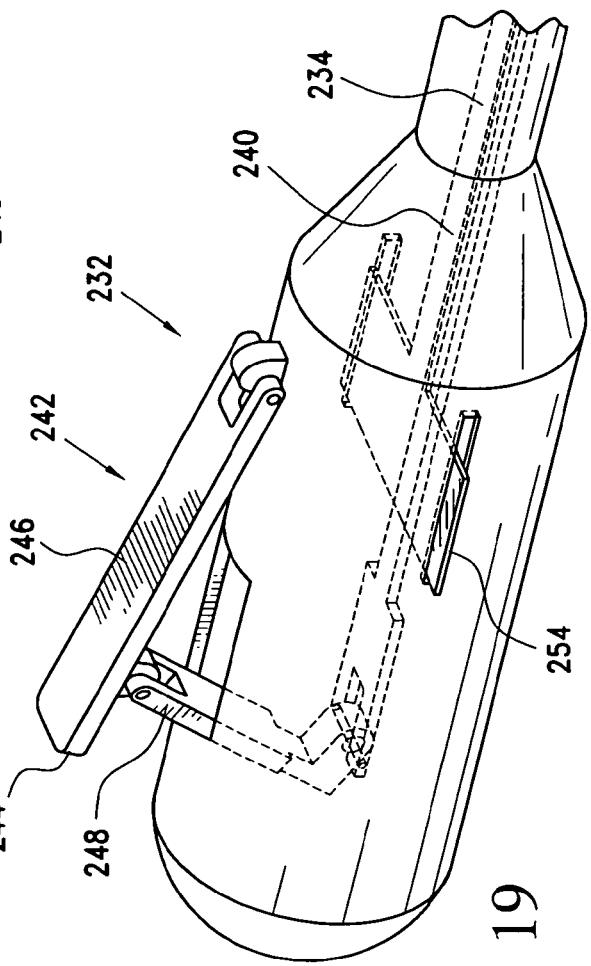
FIG. 17
FIG. 18
FIG. 19

METHOD AND APPARATUS FOR ENDOSCOPICALLY PERFORMING GASTRIC REDUCTION SURGERY IN A SINGLE PASS

BACKGROUND OF THE INVENTION

1. Field of the Invention

The present invention relates to gastric reduction surgery. More particularly, the invention relates to a method and apparatus for endoscopically performing gastric reduction surgery in a single pass.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. Currently, the most commonly performed procedure is Roux-en-Y gastric bypass (RYGB). This operation is highly complex and is commonly utilized to treat people exhibiting morbid obesity. More than 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secrete stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch, and the attached segment of duodenum, are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, post-operative recovery time can be quite lengthy and painful.

In view of the highly invasive nature of the current RYGB procedure, other less invasive procedures have been developed. One commonly employed gastric reduction procedure is vertical gastroplasty. This procedure is achieved by applying a series of sutures to create an incomplete horizontal line defining a small fundic pouch for restriction of food ingestion. This procedure is commonly performed laparoscopically and as such also requires substantial preoperative, operative, postoperative resources.

With the foregoing in mind, procedures that allow for the performance of gastric reduction surgery in a time efficient and patient friendly manner are needed. The present invention provides such a method and an associated apparatus.

SUMMARY OF THE INVENTION

It is, therefore, an object of the present invention to provide a gastric reduction apparatus which provides for the secure attachment of multiple fasteners into the gastric wall, the fasteners being linked with a flexible member in a manner permitting the reduction of the effective size of an individual's stomach. The apparatus includes an applicator head having a proximal end and a distal end. The applicator head of the gastric reduction apparatus includes a cavity shaped and dimensioned for receiving tissue. A fastener attachment mechanism is positioned within the cavity for access to tissue that is pulled within the cavity, the fastener attachment mechanism includes a plurality of fasteners.

It is also an object of the present invention to provide a method for gastric reduction surgery. The method is achieved by first inserting a gastric reduction apparatus as discussed above within the stomach. The gastric reduction apparatus is then positioned such that the opening of the cavity is adjacent a predetermined portion of the stomach wall. A vacuum is then created within the cavity drawing predetermined tissue of the stomach wall within the cavity and the fastener attachment mechanism is actuated to secure the fastener within the tissue of the stomach.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of the present gastric reduction apparatus.

FIG. 2 is a detailed view showing the present gastric reduction apparatus.

FIG. 9 is a perspective view of an alternate embodiment in accordance with the present invention.

FIG. 10 is a detailed view of the gastric reduction apparatus in accordance with the embodiment shown with reference to FIG. 9.

FIGS. 11, 12 and 13 show the steps involved in the application of fasteners in accordance with the present invention.

FIG. 14 is a perspective view showing the details of the links making up the embodiment disclosed with reference to FIG. 9.

FIGS. 15, 16, 17, 18 and 19 disclose an alternate fastener attachment mechanism in accordance with the present invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 3:
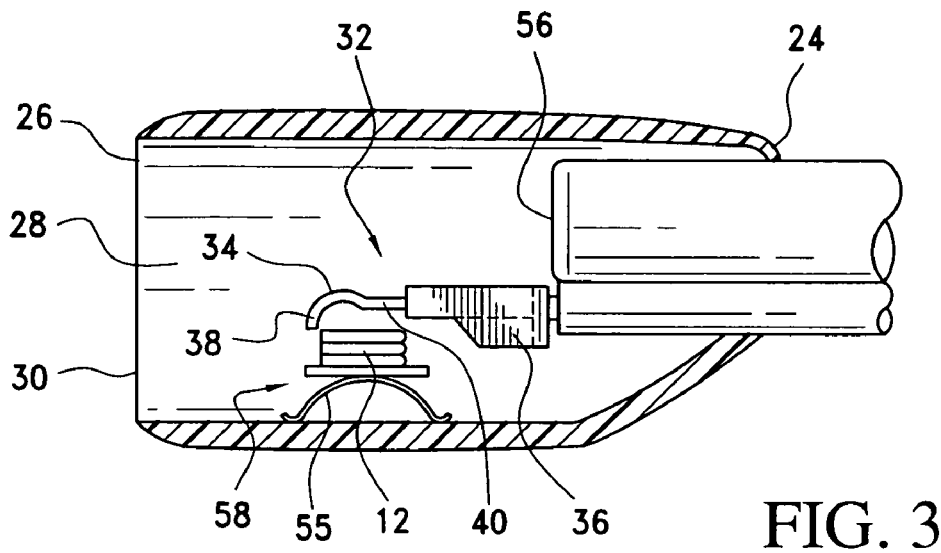
FIG. 3 is a side cross-sectional view of the present gastric reduction apparatus.
Figures 4, 5:
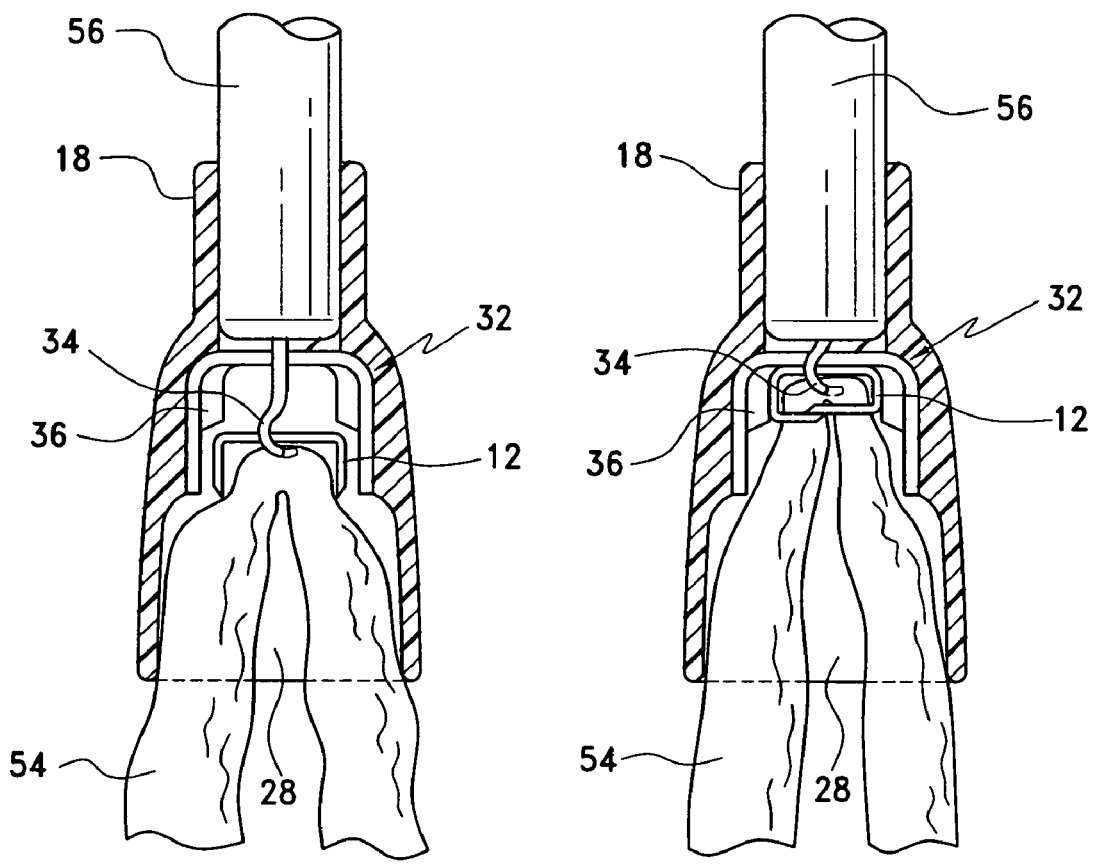
FIGS. 4, 5, 6, 7 and 8 show the application of fasteners and the formation of a stomach cavity in accordance with the present invention.
Figure 6:
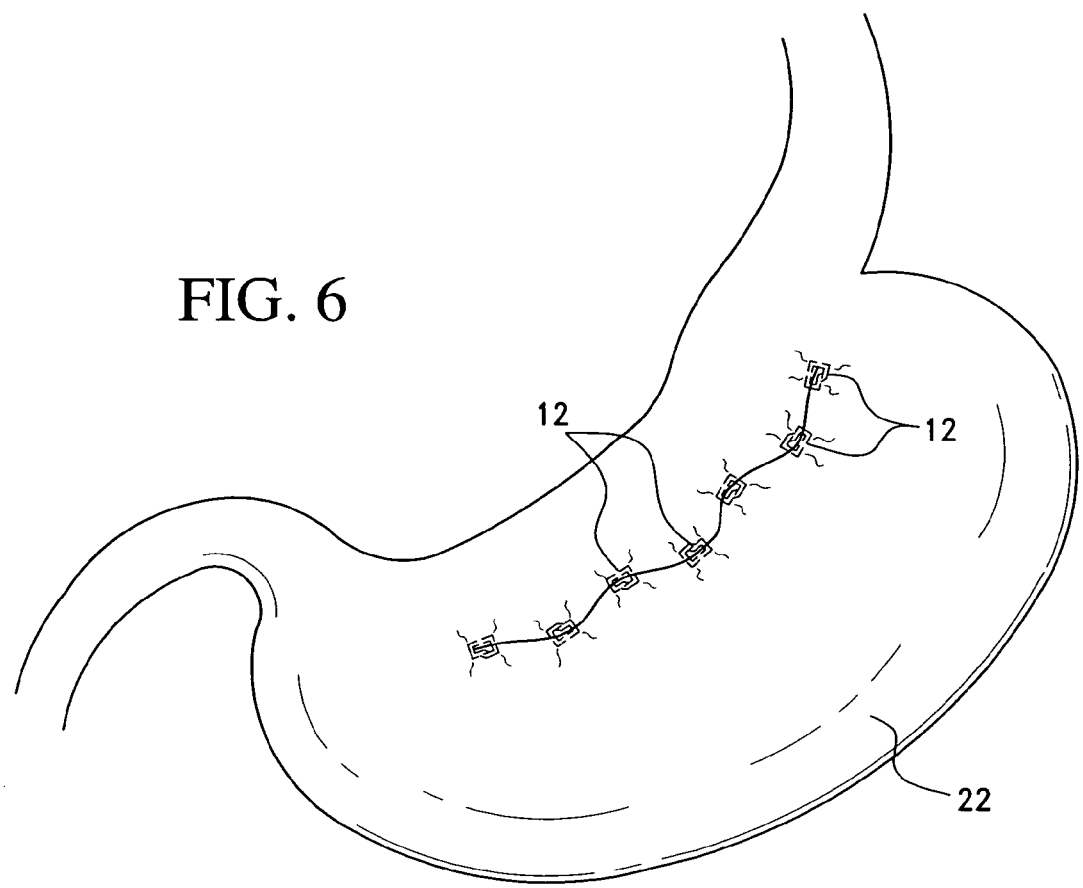
Figure 7:
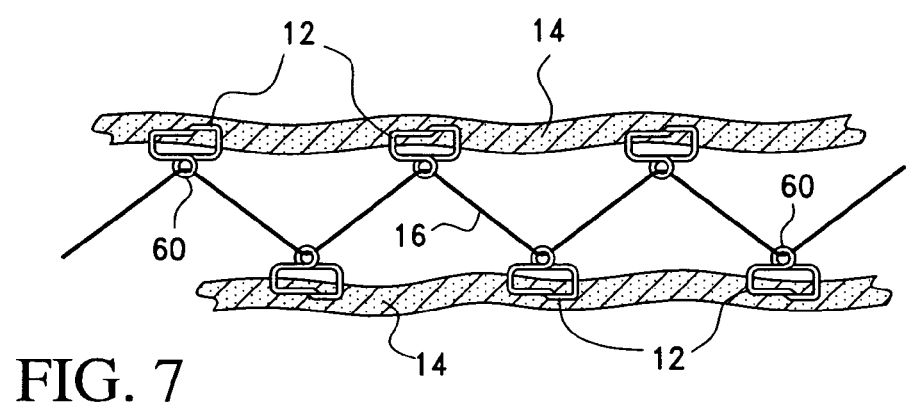
Figure 8:
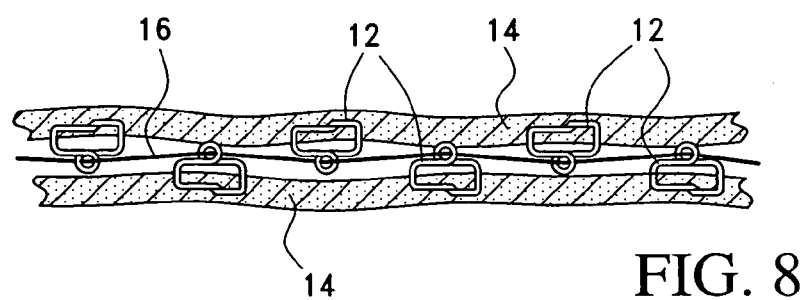

With reference to FIGS. 1 to 8, a first embodiment of an apparatus 10 and method for gastric reduction surgery is disclosed. In accordance with the invention, a gastric reduction apparatus 10 is provided which facilitates the secure attachment of multiple fasteners 12, for example, surgical staplers, into the gastric wall 14. The fasteners 12 are linked with a flexible member 16, for example, a suture, in a manner permitting the reduction of the effective size of an individual's stomach. The apparatus 10 is particularly designed for providing an improved mechanism for performing vertical gastroplasty type procedures. While the present apparatus and method have been developed with certain gastroplasty procedures in mind, the underlying concepts may be applied to a variety of temporary or permanent gastroplasty procedures.

The gastric reduction apparatus 10 is shaped and dimensioned for selective attachment to the distal end 18 of a traditional endoscopic flexible gastroscope 20. The gastric reduction apparatus 10 is manipulated utilizing cabling and suction available via the gastroscope 20 so as to position the gastric reduction apparatus 10 at a desired orientation within the stomach 22. Although the present invention is adapted for attachment to the distal end of a gastroscope, the present invention could be constructed with its own shaft without departing from the spirit of the present invention.

In particular, the gastric reduction apparatus 10 includes a proximal end 24 and a distal end 26. The proximal end 24 is shaped and dimensioned for secure attachment to the distal end 18 of the gastroscope 20. In accordance with a preferred embodiment, the proximal end 24 is secured to the gastroscope 20 using conventional coupling elements, for example, a spring clamp or elastic sleeve, which those skilled in the art will fully appreciate.

The distal end 26 of the gastric reduction apparatus 10 includes an applicator head having a cavity 28 shaped and dimensioned for receiving tissue 54 in a manner discussed below in greater detail. The cavity 28 is substantially bell-shaped providing a wide opening 30 for receiving tissue 54 for the purpose of securing fasteners 12 thereto while the tissue 54 is pulled within the cavity 28.

A fastener attachment mechanism 32 is positioned within the cavity 28 for access to tissue 54 that is pulled within the cavity 28. The fastener attachment mechanism 32 includes a plurality of fasteners 12, a hook 34 and an anvil 36. The hook 34 includes a first end 38 and a second end 40. The first end 38 of the hook 34 is shaped and dimensioned for grabbing the uppermost fastener 12 supported by the fastener attachment mechanism 32 and drawing it against the anvil 36 to close the fastener 12 in a configuration coupling the fastener 12 to the tissue 54 drawn within the cavity 28.

A leaf spring 55 serves to advance additional fasteners 12 into the ready to fire position. As the fastener attachment mechanism 32 is actuated in the manner described below, fasteners 12 are successively secured to tissue 54 drawn within the cavity 28 and each of the fasteners 12 positioned in a stack are biased toward the firing area by the leaf spring 55. When the firing area is empty, the bias of the leaf spring 55 loads the uppermost fastener 12 in the stack into the ready to fire zone, which is then ready for attachment to tissue in accordance with the principles of the present invention.

The second end 40 of the hook 34 is coupled to a firing mechanism 42 extending through the gastroscope 20. The firing mechanism 42 generally includes a cable, rod or bar 44, which extends through the gastroscope 20 to the hook 34. As such, the hook 34 is manipulated from the proximal end 46 of the gastroscope 20 via the cable 44. Manipulation of the hook 34 via the cable 44 allows the hook 34 to draw the fasteners 12 into contact with the anvil 36 in a manner discussed below in greater detail.

The firing mechanism 42 includes a lever 50 that actuates the cable 44 for drawing the hook 34 proximally in a controlled manner. More particular, the cable 44 extending through the gastroscope 20 links the hook 34 to the lever 50 which includes a handle 52 that may be actuated by a user of the present apparatus 10. By actuating the lever 50 via the handle 52, the cable 44 is moved axially drawing the hook 34 rearwardly toward the anvil 36. The rearward movement of the hook 34 draws a fastener 12 into contact with the anvil 36 in a manner that closes the fastener 12 upon the stomach tissue 54. After the lever 50 and cable 44 are moved axially, forcing the hook 34 proximally and causing the fastener 12 to form about the anvil 36, the handle 52, lever 50, cable 44 and hook 34 are returned to their initial positions via a spring bias or reverse movement of the handle 52. The fastener stack is then advanced as described previously to load the next fastener in firing apparatus.

An alternate fastener attachment mechanism 232 is disclosed with reference to FIGS. 15, 16, 17, 18 and 19. These figures specifically focus upon the fastener attachment mechanism 232 and do not show the cavity discussed above with reference to the previously disclosed embodiment, although those skilled in the art will appreciate the cavity is substantially identical to that disclosed with reference to FIGS. 1 to 8. The fastener attachment mechanism 232 includes a plurality of fasteners 212, a fastener press 234 and an anvil 236. The fastener press 234 includes a first end 238 and a second end 240. The first end 238 of the fastener press 234 includes a substantially U-shaped recess 239 which is slightly smaller than the fasteners 212 in a manner which functions to close the fasteners 212 as the first end 238 of the fastener press 234 is pushed toward the anvil 236 during actuation of the fastener attachment mechanism 232.

The forward tip 241 of the U-shaped recess 239 is shaped and dimensioned to receive the lowermost fastener 212 supported by the fastener attachment mechanism 232 and pushing it against the anvil 236 to close the fastener 212 in a configuration coupling the fastener 212 to the tissue drawn within the cavity.

As the fasteners 212 are sequentially fired and used, a leaf spring 255 serves to contain and advance additional fasteners 212 into the ready to fire position. The leaf spring 255 includes a lower surface 256 with a guide protrusion 257 forcing the fasteners 212 downwardly and forwardly for sequential engagement with the forward tip 241 of the U-shaped recess 239. As the fasteners 212 are used and the fastener press 234 is retracted to its ready position, the downward bias of the spring 255 loads the lowest fastener 212 in the stack into the ready to fire zone at the forward tip 241 of the U-shaped recess 239.

More particularly, the fastener press 234 is moved between a retracted position adapted for receiving the lowermost fastener 212 from the fastener stack and a fired position in engagement with the anvil 236. When in the retracted position, the lowermost fastener 212 is forced downward to a position adjacent the forward tip 241 of the U-shaped recess 239. Once the fastener 212 is positioned, the fastener press 234 is moved forward toward the anvil 236. This causes the fastener 212 to bend in a desired configuration. Thereafter, the fastener press 234 is retracted for receiving a new fastener 212 and the process is repeated. Controlled movement of the fastener press 234 relative to the anvil 236 is achieved by the provision of guide arms 243 which extend outwardly from the fastener press and about the support arm 245 of the anvil 236.

The second end 240 of the fastener press 234 is coupled to a firing mechanism 242 extending within the gastroscope 220. The firing mechanism 242 generally includes a linkage assembly 244 which controls the movement of the first end 238 of the fastener press 234 between its retracted position and fired position. The linkage assembly 244 generally includes an actuation lever 246 pivotally linked to a control arm 248, which is in turn pivotally linked to the second end 240 of fastener press 234. The movement of the components of the linkage assembly 244 is controlled by guides formed in the body of the handle 250 positioned at the proximal end 252 of the gastrscope 220 in a manner those skilled in the art will certainly appreciate. Control of the firing mechanism 242 is further facilitated by a lock bar 254 which interacts with the fastener press 234 to prevent actuation thereof.

Returning to the disclosure of the cavity 28 and the retention of tissue 54 therein, tissue 54 is drawn within the cavity 28 via a vacuum. More specifically, the internal space defined by the cavity 28 is in fluid communication with a vacuum line 56 extending through the gastroscope 20. In this way, one may selectively create a vacuum of sufficient strength within the cavity 28 to draw the gastric tissue 54 within the cavity 28.

In practice, the gastric reduction apparatus 10 is moved within the stomach 22 and positioned such that the opening 30 of the cavity 28 is adjacent a predetermined portion of the stomach wall 14. A vacuum is then created within the cavity 28, drawing the predetermined tissue 54 of the stomach 22 within the cavity 28.

Once the tissue 54 is fully drawn within the cavity 28, the hook 34 is actuated via the firing mechanism 42 to draw the uppermost fastener 12 off the fastener platen delivery mechanism 58. The firing mechanism 42 is then actuated to draw the cable 44 toward the proximal end 46 of the gastroscope 20, pulling the hook 34 away from the tissue 54 and into contact with the anvil 36 of the fastener attachment mechanism 32. This closes the opposite sides of the fastener 12 into the stomach tissue, securing the fastener 12 within the tissue 54 of the stomach 22.

In accordance with a preferred embodiment of the present invention, the fasteners are metal, plastic or other biocompatible materials determined to be appropriate for use in the practice of the present invention. In order to induce tissue overgrowth and thus reinforcement of the resultant line, a mesh or buttress material may be fastened between the stomach wall and the staple. This would have the net effect of distributing some of the loading over the mesh and ensuring that if one fastener were to come loose, the integrity of the entire line would not be compromised.

The process is repeated at a variety of predetermined stomach wall 14 locations. In accordance with a preferred embodiment of the present invention, the fasteners 12 are applied vertically along the stomach 22 creating a fastener arrangement necessary to ultimately form a mattress stitch pattern. The exact direction in which the fasteners are applied is not critical, and medical practitioners may apply the fasteners in a direction and order which best suits the specific patient. That is, the fasteners 12 are applied to the stomach wall 14 alternating between the anterior wall and posterior wall of the stomach 22 as the gastric reduction apparatus 10 is moved distally to proximally.

The flexible member 16 (for example, suture, ribbon) is prestrung through a connection aperture 60 within the fastener 12 and connected to the fasteners 12. The flexible member 16 is strung to create a mattress stitch pattern within the stomach 22 in a substantially vertical direction extending distally and proximally within the stomach 22. Once all of the fasteners 12 are placed along the stomach wall 14 and the flexible member 16 is strung through the connection apertures 60 of the fasteners 12 in a mattress stitch pattern, the flexible member 16 may be pulled taut to bring the gastric walls 14 into approximation with each other. Although a mattress stitch pattern is disclosed in accordance with a preferred embodiment of the present invention, other stitch patterns may be employed without departing from the spirit of the present invention.

The resulting structure of the stomach 22 is that of a tubular member connecting the esophagus to the pylorus with the gastric remnant allowed to pass gastric acid into the food stream. This produces a smaller stomach volume as well as a restrictive means for the bolus. In an alternative embodiment, the resulting structure may be that of a tubular member starting substantially at the esophagus and extending some distance toward the pylorus.

Although use of the present apparatus is disclosed with reference to the embodiment of FIGS. 1 to 8, those skilled in the art will appreciate the procedure described herein applies equally to the embodiment described with reference to FIGS. 15 to 19.

In accordance with an alternate embodiment, and with reference to FIGS. 9 to 14, the gastric reduction apparatus 110 includes its own integral shaft 162. With this in mind, the gastric reduction apparatus 110 in accordance with an alternate embodiment of the present invention includes an elongated shaft 162 having a distal end 164 and a proximal end 166. The proximal end 166 includes access to the various control mechanisms described below while the applicator head 168 is secured to the distal end 164 of the elongated shaft 162.

As with the embodiment described above with reference to FIGS. 1 to 8, the applicator head 168 includes a proximal end 124 and a distal end 126. The proximal end 124 is shaped and dimensioned for secure attachment to the elongated shaft 162 of the gastric reduction apparatus 110. The distal end 126 of the applicator head 168 includes a cavity 128 shaped and dimensioned for receiving tissue 154 in a manner discussed below in greater detail. The cavity 128 is substantially bell-shaped providing a wide opening 130 for receiving tissue 154 for the purpose of securing fasteners 112 thereto while the tissue 154 is pulled within the cavity 128.

A fastener attachment mechanism 132 is positioned within the cavity 128 for access to tissue 154, which is pulled within the cavity 128. The fastener attachment mechanism 132 includes a plurality of fasteners 112, a hook 134 and an anvil 136. The hook 134 includes a first end 138 and a second end 140. The first end 138 of the hook 134 is shaped and dimensioned for grabbing the uppermost fastener 112 supported by the fastener attachment mechanism 132 and drawing it against the anvil 136 to close the fastener 112 in a configuration coupling the fastener 112 to the tissue 154 drawn within the cavity 128.

The second end 140 of the hook 134 is coupled to a firing mechanism 142 extending through the elongated shaft 162. The firing mechanism 142 generally includes a cable 144, which extends through the elongated shaft 162 to the hook 134. As such, the hook 134 may be manipulated from the proximal end 166 of the elongated shaft 162 via the cable 144. The cable 144 links the hook 134 to an actuating switch 150 at the handle 152 of the apparatus 110 such that it may be selectively actuated by a user of the present apparatus 110. As the actuating switch 150 is drawn rearwardly, the cable 144 and the hook 134 are simultaneously drawn rearwardly. The rearward movement of the hook 134 draws the fastener 112 mounted upon the hook 134 into contact with the anvil 136 in a manner that closes the fastener 112 upon the stomach tissue 154.

As with the prior embodiment, tissue 154 is drawn within the cavity 128 via a vacuum. The internal space defined by the cavity 128 is in fluid communication with a vacuum line 156 extending through the elongated shaft 162. In this way, one may create a vacuum within the cavity 128 of sufficient strength to draw gastric tissue 154 within the cavity 128.

As briefly mentioned above, and in accordance with a preferred embodiment of the present invention, the applicator head 168 of the gastric reduction apparatus 110 is mounted at the distal end of the elongated shaft 162 which is composed of a selectively rigidized track 170. However, and as those skilled in the art will certainly appreciate, the applicator head may be mounted in other ways without departing from the spirit of the present invention.

As will be discussed below in greater detail with reference to FIG. 14, the track 170 is comprised of a series of links 176 which are all disposed on a common cable 172. In the relaxed condition, the links 176 are loosely associated with each other and the assembly can easily flex for movement around corners. When the cable 172 extending through the track 170 is tensioned, the links 176 lock together the mating features on the links causing the assembly to assume a straight configuration. The rigidized track 170 serves as a guide for the applicator head 168. By controlling the rigidity of the track 170 via a tensioning cable 172 extending between the distal and proximal ends 164, 166 of the track 170, the cable tension is selectively increased and decreased under the control of an actuating switch 174 located on the handle 152 of the present apparatus 110. The track 170 may also be selectively rotated via a pivotal connection between the track 170 and the handle 152.

With the foregoing in mind, the applicator head 168 may be rotated at a set angle to each side of the boundary between the anterior and posterior walls 114a, 114b of the stomach 122. As the applicator head 168 is moved down the rigidized track, a very repeatable zigzag pattern is established. The applicator head 168 moves down the track 170, swiveling from side to side, attaching a suture to the posterior, then anterior sides in succession. The track 170 serves to linearize the line of suturing. The rigidized track 170 helps the applicator head 168 to fire at a fixed distance from the axis of the track 170, which is the axis around which the applicator head 168 swivels.

In accordance with a preferred embodiment, the rigidized track 170 is composed of a plurality of linked track elements 176 having locking faces 178 along respective mating ends. The relative position of the track elements 176 is controlled by a tensioning cable 172 extending between the proximal and distal ends 166, 164 of the rigidized track 170. Relative flexing of the track elements 176 is achieved by providing the track elements 176 with locking faces 178 that permit flexing when the cable 172 tension is released and a rigid configuration when the cable 172 is tensioned.

In accordance with an additional feature of this embodiment, the angular displacement of the applicator head 168 to each side may be adjusted and set for each patient so as to provide some adaptability for various patient stomach sizes. Up to a limit of 180°, a wider-angle set point would result in a smaller pouch than a narrower angle set. This is because the flexible member 116 would be applied a further distance apart, allowing for more cinching. A very narrow angle set would result in a larger pouch. The axial translation of the present embodiment may be set by detents in the firing handle or on the rigidized track to standardize the longitudinal spacing of the suture angles. Closer spacing of the suture angles would result in less longitudinal shrinkage of the pouch then would be produced if greater spacing were applied.

As with the embodiment described above with reference to FIGS. 9 to 14, the gastric reduction apparatus is employed in the following manner. In practice, the applicator head 168 of the gastric reduction apparatus 110 is moved within the stomach 122 and positioned such that the opening 130 of the cavity 128 is adjacent a predetermined portion of the stomach wall 114. A vacuum is then created within the cavity 128, drawing the predetermined tissue 154 of the stomach wall 114 within the cavity.

Once the tissue 154 is fully drawn within the cavity 128, the hook 134 is actuated via the firing mechanism 142 to draw the uppermost fastener 112 off the fastener platen delivery mechanism 158. The firing mechanism 142 is then actuated to draw the cable 144 toward the proximal end 166 of the elongated shaft 162 and pull the hook 134 away from the tissue 154 and into contact with the anvil 136 of the fastener attachment mechanism 132. This closes the opposite sides of the fastener 112 into the stomach wall 114, securing the fastener 112 within the tissue 154 of the stomach wall 114.

The process is repeated at a variety of predetermined stomach wall locations moving the applicator head 168 anteriorly and posteriorly under the control of the rigidized track 170. In accordance with a preferred embodiment of the present invention, the fasteners 112 are applied vertically along the stomach 122 creating a fastener arrangement necessary to ultimately form a mattress stitch pattern. That is, the fasteners 112 are applied to the stomach wall 114 alternating between the anterior walls 114a and posterior walls 114b of the stomach 122 as the gastric reduction apparatus 110 is moved distally to proximally.

As with embodiment disclosed above, the flexible member 116 is prestrung through connection apertures 160 within the respective fastener 112, and connected to, the fasteners 112. As a result, a mattress stitch pattern is created within the stomach 122 in a substantially vertical direction extending distally and proximally within the stomach 122. Once all of the fasteners 112 are placed along the stomach wall 114 and the flexible member 116 is strung within the fasteners 112 in a mattress stitch pattern, the flexible member 116 may be pulled taut to bring the gastric walls 114 into approximation with each other.

Although a preferred firing mechanism is disclosed above, it is contemplated that advances in technology may permit the firing mechanism to be positioned adjacent the fastener application mechanism. This will allow for the greater transmission of force to the fastener application mechanism without requiring the force be transmitted along the endoscope. More particularly, electroactive polymer technology may be employed adjacent the distal end of the fastener application mechanism to draw the hook within the anvil for closing the fasteners.

Electroactive polymers are essentially capacitors, with thin conductive sheets, most recently, carbon fiber composites laminated onto a polymer core. A very low voltage, in the neighborhood of 1.5 to 3.3 volts is induced across the electrodes. This draws the electrodes together, causing deformation of the polymer between the electrodes. The effect causes a change in the shape of a polymer much in the same way that a human muscle works. The end result is an expansion of the polymer in one direction and a contraction in the perpendicular direction. When one employs many sheets stacked together an additive forced generation is achieved. It is this contraction that results in a tensile load on any structure to which the electroactive polymer bundle is attached.

It is contemplated such an embodiment would be implemented by using the electroactive polymers to connect the hook and the anvil. The anvil would serve as a mechanical ground to which the electroactive polymer strip is attached. As a voltage is placed across the electroactive polymer laminate structure, the contraction of the strip in the device longitudinal direction would pull the hook back proximally, causing the staple to close due to the interaction with the anvil.

In creating optimum strength it is important that the sheet be very thin (20 microns) to optimize the output force. The result of stacking these sheets results in high force output "motors" with an available power density of 200 kg/cm^2, approximately 100 times the power density of a human muscle. Given the availability of this power source in accordance with an alternate embodiment, the electroactive polymers may be utilized to deliver a load at the needed position within the fastener attachment mechanism without dissipating fastening energy along components of the gastroscope as the cable transmits force from the handle to the applicator head. Implementation of the electroactive polymers will greatly simplify the design requirements of the present apparatus. In addition, the reduced shaft load will allow for the production of a less costly gastric reduction apparatus.

It is further contemplated that glues may be used to enhance the seal created in accordance with the present apparatus The glue would be a fibrin based glue such as is commercially available from companies such as Ethicon Inc. Such a glue would be applied separately from this device along the line just prior to cinching down the line. The presence of the glue would reduce tension on the line during the critical two week healing process and lengthen the effective duration of the line.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A gastric reduction apparatus which provides for the secure attachment of multiple fasteners into the gastric wall, the fasteners being linked with a flexible member in a manner permitting the reduction of the effective size of an individual's stomach, comprising:
the gastric reduction apparatus including a proximal end and a distal end, the apparatus including a vacuum line in fluid communication with an applicator head at the distal end of the gastric reduction apparatus;
the applicator head having a cavity defining an internal space and including a wide opening shaped and dimensioned for receiving tissue, the internal space defined by the cavity is in fluid communication with the vacuum line;
a fastener attachment mechanism is positioned within the cavity for access to tissue that is pulled within the cavity, the fastener attachment mechanism includes at least one fastener, a hook and an anvil, the hook including a first end and a second end, the first end being shaped and dimensioned for grabbing the fastener and the second end being coupled to a firing mechanism for controlling contact of the fastener with the anvil.

2. The gastric reduction apparatus according to claim 1, wherein the proximal end is shaped and dimensioned for secure attachment to a distal end of a gastroscope.

3. The gastric reduction apparatus according to claim 1, wherein the cavity is substantially bell-shaped providing the wide opening for receiving tissue for the purpose of securing fasteners thereto while the tissue is pulled within the cavity.

4. The gastric reduction apparatus according to claim 1, wherein the fastener attachment mechanism includes a firing mechanism composed of electroactive polymers.

5. The gastric reduction apparatus according to claim 1, wherein the first end of the hook is shaped and dimensioned for grabbing an uppermost fastener supported by the fastener attachment mechanism and drawing it against the anvil to close the fastener in a configuration coupling the fastener to the tissue drawn within the cavity.

6. The gastric reduction apparatus according to claim 5, wherein the firing mechanism includes a cable, bar, or rod that extends to the hook allowing the hook to be manipulated.

7. The gastric reduction apparatus according to claim 5, wherein the firing mechanism further includes a mechanism, which draws the hook proximally in a controlled manner.

8. The gastric reduction apparatus according to claim 1, wherein the apparatus includes an elongated shaft which runs down along the side of a gastroscope, the shaft includes a proximal end and a distal end, the proximal end including access to control mechanisms of the fastener attachment mechanism and the applicator head is secured to the distal end of the elongated shaft.

9. The gastric reduction apparatus according to claim 8, wherein the elongated shaft is composed of a selectively rigidized track.

10. The gastric reduction apparatus according to claim 9, wherein the track is composed of a plurality of links disposed on a common cable.

11. The gastric reduction apparatus according to claim 10, wherein the links are loosely associated with each other and controlled via a tensioning cable extending between the distal end and proximal end of the track.

12. The gastric reduction apparatus according to claim 10, wherein the track is rotatable via a pivotal connection between the track and a handle.

13. The gastric reduction apparatus according to claim 10, wherein the plurality of links have locking faces along respective mating ends.

14. A gastric reduction apparatus which provides for the secure attachment of multiple fasteners into the gastric wall, the fasteners being linked with a flexible member in a manner permitting the reduction of the effective size of an individual's stomach, comprising:
the gastric reduction apparatus including a proximal end and a distal end, the apparatus including a vacuum line in fluid communication with an applicator head at the distal end of the gastric reduction apparatus;
the applicator head having a cavity defining an internal space and including a wide opening shaped and dimensioned for receiving tissue, the internal space defined by the cavity is in fluid communication with the vacuum line;
a fastener attachment mechanism is positioned within the cavity for access to tissue that is pulled within the cavity, the fastener attachment mechanism includes at least one fastener, a fastener press and anvil wherein the fastener press receives a fastener and then moves the fastener into contact with the anvil, the fastener attachment mechanism further including a linkage assembly for moving the fastener press between a retracted position and fired position.

15. The gastric reduction apparatus according to claim 14, wherein the proximal end is shaped and dimensioned for secure attachment to a distal end of a gastroscope.

16. The gastric reduction apparatus according to claim 14, wherein the cavity is substantially bell-shaped providing the wide opening for receiving tissue for the purpose of securing fasteners thereto while the tissue is pulled within the cavity.

17. The gastric reduction apparatus according to claim 14, wherein the fastener attachment mechanism includes a firing mechanism composed of electroactive polymers.

18. The gastric reduction, apparatus according to claim 14, wherein the apparatus includes an elongated shaft which runs down along the side of a gastroscope, the shaft includes a proximal end and a distal end, the proximal end including access to control mechanisms of the fastener attachment mechanism and the applicator head is secured to the distal end of the elongated shaft.

19. The gastric reduction apparatus according to claim 18, wherein the elongated shaft is composed of a selectively rigidized track.

20. The gastric reduction apparatus according to claim 19, wherein the track is composed of a plurality of links disposed on a common cable.

21. The gastric reduction apparatus according to claim 20, wherein the links are loosely associated with each other and controlled via a tensioning cable extending between the distal end and proximal end of the track.

22. The gastric reduction apparatus according to claim 20, wherein the track is rotatable via a pivotal connection between the track and a handle.

23. The gastric reduction apparatus according to claim 20, wherein the plurality of links have locking faces along respective mating ends.

* * * * *